United States Patent
Frøstrup et al.

(10) Patent No.: US 7,700,619 B2
(45) Date of Patent: Apr. 20, 2010

(54) 2-METHOXYMETHYL-3-(3,4-DICHLOROPHENYL)-8-AZABICYCLO[3.2.1]OCTANE TARTRATE SALTS

(75) Inventors: Brian Frøstrup, Ballerup (DK); Frank Wätjen, Ballerup (DK); Klaus Snej Jensen, Frederiksberg C (DK)

(73) Assignee: Neurosearch A/S, Ballerup (DK)

( * ) Notice: Subject to any disclaimer, the term of this patent is extended or adjusted under 35 U.S.C. 154(b) by 584 days.

(21) Appl. No.: 10/566,384

(22) PCT Filed: Jul. 29, 2004

(86) PCT No.: PCT/EP2004/051651

§ 371 (c)(1),
(2), (4) Date: Jan. 30, 2006

(87) PCT Pub. No.: WO2005/011694

PCT Pub. Date: Feb. 10, 2005

(65) Prior Publication Data

US 2007/0043075 A1    Feb. 22, 2007

Related U.S. Application Data

(60) Provisional application No. 60/494,090, filed on Aug. 12, 2003.

(30) Foreign Application Priority Data

Jul. 31, 2003    (DK) ................................ 2003 01117

(51) Int. Cl.
   *A01N 43/42* (2006.01)
(52) U.S. Cl. ...................................... 514/304; 546/124
(58) Field of Classification Search ................. 514/304; 546/124
   See application file for complete search history.

(56) References Cited

U.S. PATENT DOCUMENTS 6,288,079 B1 * 9/2001 Scheel-Kruger et al. .... 514/304

FOREIGN PATENT DOCUMENTS

WO    WO-97/30997 A    8/1997
WO    WO-03/045388 A1    6/2003

OTHER PUBLICATIONS

Berge et al. Pharmaceutical Salts. J. Pharm. Science. 1977;66(1):1-19.*
Keverline-Frantz et al., J. Med. Chem. vol. 41, No. 2, 1998, pp. 247-257. XP002311009.

* cited by examiner

*Primary Examiner*—James O Wilson
*Assistant Examiner*—Valerie Rodriguez-Garcia
(74) *Attorney, Agent, or Firm*—Birch, Stewart, Kolasch & Birch, LLP

(57) ABSTRACT

This invention relates to novel (1R,2R,3S,5S)-2-methoxymethyl-3-(3,4-dichlorophenyl)-8-azabicyclo[3.2.1]octane tartrate salts, such as L-tartrate monohydrates and anhydrates, wherein the salts are useful as monoamine neurotransmitter re-uptake inhibitors. Additionally, the invention also relates to the use of these salts in a method for therapy and to pharmaceutical compositions comprising the salts of the invention.

2 Claims, No Drawings

2-METHOXYMETHYL-3-(3,4-DICHLOROPHENYL)-8-AZABICYCLO[3.2.1]OCTANE TARTRATE SALTS

This National Phase PCT application claims priority under 35 U.S.C. 119(a) on Patent Application No(s). PA 2003 01117 filed in Denmark on Jul. 31, 2003, and under 35 U.S.C. 119(e) on U.S. Provisional Application No. 60/494,090 filed on Aug. 12, 2003, all of which are hereby incorporated by reference.

TECHNICAL FIELD

This invention relates to novel (1R,2R,3S,5S)-2-methoxymethyl-3-(3,4-dichlorophenyl)-8-azabicyclo[3.2.1]octane tartrate salts, such as L-tartrate monohydrates and anhydrates. The salts are useful as monoamine neurotransmitter re-uptake inhibitors.

In other aspects the invention relates to the use of these salts in a method for therapy and to pharmaceutical compositions comprising the salts of the invention.

BACKGROUND ART

The compound (1R,2R,3S,5S)-2-methoxymethyl-3-(3,4-dichlorophenyl)-8-azabicyclo[3.2.1]octane is disclosed in WO 97/30997 (NeuroSearch A/S). Therein, the citrate salt was prepared (Example 15).

For commercial use, however, it is important to have a physiologically acceptable salt with an optimal combination of stability, solubility, non-hygroscopicity, bioavailablity and good handling properties, such as a well defined melting point and a reproducible crystalline form.

SUMMARY OF THE INVENTION

In its first aspect, the invention provides a salt selected from the anhydrous and hydrated forms of (1R,2R,3S,5S)-2-methoxymethyl-3-(3,4-dichlorophenyl)-8-azabicyclo[3.2.1]octane tartrate.

In its second aspect, the invention provides a pharmaceutical composition, comprising a therapeutically effective amount of a salt of the invention, together with at least one pharmaceutically acceptable carrier, excipient or diluent.

In a further aspect, the invention provides the use of a salt of the invention, for the manufacture of a pharmaceutical composition for the treatment, prevention or alleviation of a disease or a disorder or a condition of a mammal, including a human, which disease, disorder or condition is responsive to inhibition of monoamine neurotransmitter re-uptake in the central nervous system.

In a still further aspect, the invention relates to a method for treatment, prevention or alleviation of a disease or a disorder or a condition of a living animal body, including a human, which disorder, disease or condition is responsive to responsive to inhibition of monoamine neurotransmitter re-uptake in the central nervous system, which method comprises the step of administering to such a living animal body in need thereof a therapeutically effective amount of a salt of the invention.

Other objects of the invention will be apparent to the person skilled in the art from the following detailed description and examples.

DETAILED DISCLOSURE OF THE INVENTION (1R,2R,3S,5S)-2-methoxymethyl-3-(3,4-dichlorophenyl)-8-azabicyclo[3.2.1]octane tartrate In its first aspect the present invention provides a salt selected from the anhydrous and hydrated forms of (1R,2R,3S,5S)-2-methoxymethyl-3-(3,4-dichlorophenyl)-8-azabicyclo[3.2.1]octane tartrate.

In one embodiment, the salt is selected from the anhydrous and hydrated forms of (1R,2R,3S,5S)-2-methoxymethyl-3-(3,4-dichlorophenyl)-8-azabicyclo[3.2.1]octane L-tartrate.

In a second embodiment, the salt is (1R,2R,3S,5S)-2-methoxymethyl-3-(3,4-dichlorophenyl)-8-azabicyclo[3.2.1]octane L-tartrate monohydrate.

In a further embodiment, the salt is an anhydrous form of (1R,2R,3S,5S)-2-methoxymethyl-3-(3,4-dichlorophenyl)-8-azabicyclo[3.2.1]octane L-tartrate.

In a still further embodiment, the salt is the polymorphic form (form II) of (1R,2R,3S,5S)-2-methoxymethyl-3-(3,4-dichlorophenyl)-8-azabicyclo[3.2.1]octane L-tartrate anhydrate characterized by the following principal peaks in its X-ray powder diffraction pattern:

|  | Peak No. | | | | | | | | | |
| --- | --- | --- | --- | --- | --- | --- | --- | --- | --- | --- |
|  | 1 | 2 | 3 | 4 | 5 | 6 | 7 | 8 | 9 | 10 |
| 2 Theta ° (Cu Kα) | 10.35 | 11.68 | 12.53 | 14.81 | 15 | 15.77 | 16.82 | 17.41 | 17.77 | 18.87 |
| d space (Å) | 8.5 | 7.6 | 7.1 | 6.0 | 5.9 | 5.6 | 5.3 | 5.1 | 5.0 | 4.7 |

|  | Peak | | | | | | | | |
| --- | --- | --- | --- | --- | --- | --- | --- | --- | --- |
|  | 11 | 12 | 13 | 14 | 15 | 16 | 17 | 18 | 19 |
| 2 Theta ° (Cu Kα) | 20.29 | 21.26 | 21.66 | 23.44 | 23.73 | 25.44 | 25.99 | 27.58 | 28.14 |
| d space (Å) | 4.4 | 4.2 | 4.1 | 3.8 | 3.7 | 3.5 | 3.4 | 3.2 | 3.2 |

In a further embodiment, the salt is the polymorphic form (form III) of (1R,2R,3S,5S)-2-methoxymethyl-3-(3,4-dichlorophenyl)-8-azabicyclo[3.2.1]octane L-tartrate anhydrate characterized by the following principal peaks in its X-ray powder diffraction pattern:

| | Peak No. | | | | | | | | | |
|---|---|---|---|---|---|---|---|---|---|---|
| | 1 | 2 | 3 | 4 | 5 | 6 | 7 | 8 | 9 | 10 |
| 2 Theta ° (Cu Kα) | 5.37 | 10.6 | 10.82 | 11.58 | 11.88 | 12.79 | 14.78 | 16.27 | 16.5 | 17.03 |
| d space (Å) | 16.4 | 8.3 | 8.2 | 7.6 | 7.4 | 6.9 | 6.0 | 5.4 | 5.4 | 5.2 |

| | Peak | | | | | | | | |
|---|---|---|---|---|---|---|---|---|---|
| | 11 | 12 | 13 | 14 | 15 | 16 | 17 | 18 | 19 |
| 2 Theta ° (Cu Kα) | 17.84 | 19.29 | 20.01 | 21.2 | 22.99 | 23.46 | 24.54 | 25.15 | 26.59 |
| d space (Å) | 5.0 | 4.6 | 4.4 | 4.2 | 3.9 | 3.8 | 3.6 | 3.5 | 3.3 |

In a still further embodiment, the salt is the polymorphic form (form IV) of (1R,2R,3S,5S)-2-methoxymethyl-3-(3,4-dichlorophenyl)-8-azabicyclo[3.2.1]octane L-tartrate anhydrate characterized by the following principal peaks in its X-ray powder diffraction pattern:

| | Peak No. | | | | | | | | | |
|---|---|---|---|---|---|---|---|---|---|---|
| | 1 | 2 | 3 | 4 | 5 | 6 | 7 | 8 | 9 | 10 |
| 2 Theta ° (Cu Kα) | 5.31 | 10.19 | 11.23 | 12.13 | 12.35 | 12.69 | 14.31 | 14.55 | 14.77 | 16.43 |
| d space (Å) | 16.6 | 8.7 | 7.9 | 7.3 | 7.2 | 7.0 | 6.2 | 6.1 | 6.0 | 5.4 |

| | Peak | | | | | | | | | |
|---|---|---|---|---|---|---|---|---|---|---|
| | 11 | 12 | 13 | 14 | 15 | 16 | 17 | 18 | 19 | 20 |
| 2 Theta ° (Cu Kα) | 17.48 | 18.21 | 18.43 | 18.81 | 19.36 | 19.61 | 20.26 | 20.5 | 21.29 | 21.46 |
| d space (Å) | 5.1 | 4.9 | 4.8 | 4.7 | 4.6 | 4.5 | 4.4 | 4.3 | 4.2 | 4.1 |

| | Peak | | | | | | | | | | |
|---|---|---|---|---|---|---|---|---|---|---|---|
| | 21 | 22 | 23 | 24 | 25 | 26 | 27 | 28 | 29 | 30 | 31 | 32 |
| 2 Theta ° (Cu Kα) | 21.95 | 22.53 | 22.77 | 23.38 | 23.59 | 23.9 | 24.45 | 25.02 | 25.56 | 26.19 | 26.83 | 27.21 |
| d space (Å) | 4.0 | 3.9 | 3.9 | 3.8 | 3.8 | 3.7 | 3.6 | 3.6 | 3.5 | 3.4 | 3.3 | 3.3 |

Any combination of two or more of the embodiments as described above is considered within the scope of the present invention.

Hydrated Forms

The salt of the invention may be provided in anhydrous forms or hydrated forms. Hydrated forms include the monohydrate, the dihydrate, the hemihydrate, the trihydrate, the tetrahydrate, and the like.

Labelled Compounds

The salts of the invention may be used in their labelled or unlabelled form. In the context of this invention "label" stands for the binding of a marker to the salt of interest that will allow easy quantitative detection of said salt.

The labelled salts of the invention may be useful as diagnostic tools, radio tracers, or monitoring agents in various diagnostic methods, and for in vivo receptor imaging.

The labelled salt of the invention preferably contains at least one radionuclide as a label. Positron emitting radionuclides are all candidates for usage. In the context of this invention the radionuclide is preferably selected from $^2$H (deuterium), $^3$H (tritium), $^{13}$C, and $^{14}$C.

Methods of Preparation

The salts of the invention may be prepared by conventional methods for chemical synthesis, e.g. those described in the working examples. The starting materials for the processes described in the present application are known or may readily be prepared by conventional methods from commercially available chemicals.

Also one salt of the invention can be converted to another salt of the invention using conventional methods.

The end products of the reactions described herein may be isolated by conventional techniques, e.g. by extraction, crystallisation, distillation, chromatography, etc.

Biological Activity

Salts of the invention may be tested for their ability to inhibit reuptake of the monoamines dopamine, noradrenaline and serotonin in synaptosomes eg such as described in WO 97/30997. Based on the balanced activity observed in these tests the salts of the invention is considered useful for the treatment the treatment, prevention or alleviation of a disease or a disorder or a condition of a mammal, including a human, which disease, disorder or condition is responsive to inhibition of monoamine neurotransmitter re-uptake in the central nervous system.

In a special embodiment, the salts of the invention are considered useful for the treatment, prevention or alleviation of: mood disorder, depression, atypical depression, depression secondary to pain, major depressive disorder, dysthymic disorder, bipolar disorder, bipolar I disorder, bipolar II disorder, cyclothymic disorder, mood disorder due to a general medical condition, substance-induced mood disorder, pseudodementia, Ganser's syndrome, obsessive compulsive disorder, panic disorder, panic disorder without agoraphobia, panic disorder with agoraphobia, agoraphobia without history of panic disorder, panic attack, memory deficits, memory loss, attention deficit hyperactivity disorder, obesity, anxiety, generalized anxiety disorder, eating disorder, Parkinson's disease, parkinsonism, dementia, dementia of ageing, senile dementia, Alzheimer's disease, acquired immunodeficiency syndrome dementia complex, memory dysfunction in ageing, specific phobia, social phobia, post-traumatic stress disorder, acute stress disorder, drug addiction, drug abuse, cocaine abuse, nicotine abuse, tobacco abuse, alcohol addiction, alcoholism, pain, chronic pain, inflammatory pain, neuropathic pain, migraine pain, tension-type headache, chronic tension-type headache, pain associated with depression, fibromyalgia, arthritis, osteoarthritis, rheumatoid arthritis, back pain, cancer pain, irritable bowel pain, irritable bowel syndrome, post-operative pain, post-stroke pain, drug-induced neuropathy, diabetic neuropathy, sympathetically-maintained pain, trigeminal neuralgia, dental pain, myofacial pain, phantom-limb pain, bulimia, premenstrual syndrome, late luteal phase syndrome, post-traumatic syndrome, chronic fatigue syndrome, urinary incontinence, stress incontinence, urge incontinence, nocturnal incontinence, sexual dysfunction, premature ejaculation, erectile difficulty, erectile dysfunction, eating disorders, anorexia nervosa, sleep disorders, autism, mutism, trichotillomania, narcolepsy, post-stroke depression, stroke-induced brain damage, stroke-induced neuronal damage or Gilles de la Tourettes disease.

It is at present contemplated that a suitable dosage of the active pharmaceutical ingredient (API) is within the range of from about 0.1 to about 100 mg API per day, more preferred of from about 0.1 to about 10 mg API per day, most preferred of from about 0.5 to about 5 mg API per day, dependent, however, upon the exact mode of administration, the form in which it is administered, the indication considered, the subject and in particular the body weight of the subject involved, and further the preference and experience of the physician or veterinarian in charge.

Pharmaceutical Compositions

In another aspect the invention provides novel pharmaceutical compositions comprising a therapeutically effective amount of the salt of the invention.

While a salt of the invention for use in therapy may be administered in the form of the raw salt, it is preferred to introduce the active ingredient, in a pharmaceutical composition together with one or more adjuvants, excipients, carriers, buffers, diluents, and/or other customary pharmaceutical auxiliaries.

In a preferred embodiment, the invention provides pharmaceutical compositions comprising the salt of the invention, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the salt of the invention, which matrices may be in form of shaped articles, e.g. films or microcapsules.

The salt of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The salt of the present invention can be administered in a wide variety of oral and parenteral dosage forms.

For preparing pharmaceutical compositions from a salt of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The salt according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations, intended for conversion shortly before use to liquid form preparations for oral administration. Such liquid forms include solutions, suspensions, and emulsions. In addition to the active component such preparations may comprise colorants, flavours, stabilisers, buffers, artificial and natural sweeteners, dispersants, thickeners, solubilizing agents, and the like.

For topical administration to the epidermis the salt of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the salt in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the active compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

A therapeutically effective dose refers to that amount of active ingredient, which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions exhibiting large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depend on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 10 mg of active ingredient per individual dose, preferably of from about 0.5 to about 5 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

In another aspect the invention provides a method for the treatment, prevention or alleviation of a disease or a disorder or a condition of a living animal body, including a human, which disease, disorder or condition is responsive to inhibition of monoamine neurotransmitter re-uptake in the central nervous system, and which method comprises administering to such a living animal body, including a human, in need thereof an effective amount of a salt of the invention.

Suitable dosage ranges are dependent as usual upon the exact mode of administration, form in which administered, the indication toward which the administration is directed, the subject involved and the body weight of the subject involved, and further the preference and experience of the physician or veterinarian in charge.

EXAMPLES

The invention is further illustrated with reference to the following examples, which are not intended to be in any way limiting to the scope of the invention as claimed.

Example 1

(1R,2R,3S,5S)-2-methoxymethyl-3-(3,4-dichlorophenyl)-8-azabicyclo[3.2.1]octane citrate salt The citrate salt of (1R,2R,3S,5S)-2-methoxymethyl-3-(3,4-dichlorophenyl)-8-azabicyclo[3.2.1]octane was synthesized as described in WO 97/30997 (Example 15).

(1R,2R,3S,5S)-2-methoxymethyl-3-(3,4-dichlorophenyl)-8-azabicyclo[3.2.1]octane

The free base was obtained from dissolving the citrate salt in water and adjusting pH to 10-13 with aqueous base, followed with extraction with toluene. The toluene phase was collected, dried end evaporated to dryness. This left the free base as an oil.

Example 2

(1R,2R,3S,5S)-2-methoxymethyl-3-(3,4-dichlorophenyl)-8-azabicyclo[3.2.1]octane L-tartrate monohydrate (Form I)

To a heated solution of (1R,2R,3S,5S)-2-methoxymethyl-3-(3,4-dichlorophenyl)-8-azabicyclo[3.2.1]octane (the free base) in aqueous ethanol was added L-tartaric acid. The warm mixture was treated with activated charcoal and filtered. The filtrate was cooled and (1R,2R,3S,5S)-2-methoxymethyl-3-(3,4-dichlorophenyl)-8-azabicyclo-[3.2.1]octane was isolated as the L-tartrate monohydrate.

Form I is characterized by the following principal peaks in its X-ray powder diffraction pattern shown below:

|  | Peak No. | | | | | | | | | |
|---|---|---|---|---|---|---|---|---|---|---|
|  | 1 | 2 | 3 | 4 | 5 | 6 | 7 | 8 | 9 | 10 |
| 2 Theta ° (Cu Kα) | 12.05 | 14.21 | 16.37 | 17.4 | 18.34 | 19.29 | 19.58 | 20.27 | 23.3 | 23.75 |
| d space (Å) | 7.3 | 6.2 | 5.4 | 5.1 | 4.8 | 4.6 | 4.5 | 4.4 | 3.8 | 3.7 |
|  | Peak | | | | | | |
|  | 11 | 12 | 13 | 14 | 15 | 16 | 17 |
| 2 Theta ° (Cu Kα) | 24.37 | 26.11 | 26.76 | 28.25 | 28.72 | 29.25 | 29.82 |
| d space (Å) | 3.6 | 3.4 | 3.3 | 3.2 | 3.1 | 3.1 | 3.0 |

Example 3

(1R,2R,3S,5S)-2-methoxymethyl-3-(3,4-dichlorophenyl)-8-azabicyclo[3.2.1]octane L-tartrate anhydrate (Form II)

The form was prepared thermal dehydration. (1R,2R,3S,5S)-2-methoxymethyl-3-(3,4-dichlorophenyl)-8-azabicyclo[3.2.1]octane L-tartrate monohydrate (Form I) was heated in a TGA $AlO_2$ crucible to 125° C., 10° C./min. The salt was allowed to cool before opening the TGA furnace. During heating and cooling the furnace was purged with 50 ml/min dry nitrogen.

Form II is characterized by the following principal peaks in its X-ray powder diffraction pattern shown below:

| | Peak No. | | | | | | | | | |
|---|---|---|---|---|---|---|---|---|---|---|
| | 1 | 2 | 3 | 4 | 5 | 6 | 7 | 8 | 9 | 10 |
| 2 Theta ° (Cu Kα) | 10.35 | 11.68 | 12.53 | 14.81 | 15 | 15.77 | 16.82 | 17.41 | 17.77 | 18.87 |
| d space (Å) | 8.5 | 7.6 | 7.1 | 6.0 | 5.9 | 5.6 | 5.3 | 5.1 | 5.0 | 4.7 |

| | Peak | | | | | | | | |
|---|---|---|---|---|---|---|---|---|---|
| | 11 | 12 | 13 | 14 | 15 | 16 | 17 | 18 | 19 |
| 2 Theta ° (Cu Kα) | 20.29 | 21.26 | 21.66 | 23.44 | 23.73 | 25.44 | 25.99 | 27.58 | 28.14 |
| d space (Å) | 4.4 | 4.2 | 4.1 | 3.8 | 3.7 | 3.5 | 3.4 | 3.2 | 3.2 |

Example 4

(1R,2R,3S,5S)-2-methoxymethyl-3-(3,4-dichlorophenyl)-8-azabicyclo[3.2.1]octane L-tartrate anhydrate (Form III)

The form was prepared thermal dehydration. (1R,2R,3S,5S)-2-methoxymethyl-3-(3,4-dichlorophenyl)-8-azabicyclo[3.2.1]octane L-tartrate monohydrate (Form I) was heated in a TGA $AlO_2$ crucible to 160° C., 10° C./min. The salt was allowed to cool before opening the TGA furnace. During heating and cooling the furnace was purged with 50 ml/min dry nitrogen.

Form III is characterized by the following principal peaks in its X-ray powder diffraction pattern shown below:

| | Peak No. | | | | | | | | | |
|---|---|---|---|---|---|---|---|---|---|---|
| | 1 | 2 | 3 | 4 | 5 | 6 | 7 | 8 | 9 | 10 |
| 2 Theta ° (Cu Kα) | 5.37 | 10.6 | 10.82 | 11.58 | 11.88 | 12.79 | 14.78 | 16.27 | 16.5 | 17.03 |
| d space (Å) | 16.4 | 8.3 | 8.2 | 7.6 | 7.4 | 6.9 | 6.0 | 5.4 | 5.4 | 5.2 |

| | Peak | | | | | | | | |
|---|---|---|---|---|---|---|---|---|---|
| | 11 | 12 | 13 | 14 | 15 | 16 | 17 | 18 | 19 |
| 2 Theta ° (Cu Kα) | 17.84 | 19.29 | 20.01 | 21.2 | 22.99 | 23.46 | 24.54 | 25.15 | 26.59 |
| d space (Å) | 5.0 | 4.6 | 4.4 | 4.2 | 3.9 | 3.8 | 3.6 | 3.5 | 3.3 |

Example 5

(1R,2R,3S,5S)-2-methoxymethyl-3-(3,4-dichlorophenyl)-8-azabicyclo[3.2.1]octane L-tartrate anhydrate (Form IV)

The form was prepared by suspending a freshly prepared Form II in water free ethanol. Separation of the suspended matter was conducted after 24 hours and subsequent drying under vacuum.

Form IV can also be obtained from suspension of Form III by the same procedure as described using Form II.

Apparently Form IV was physically metastable. Successive preparations of Form IV turned out as mixtures of Form IV and Form III, indicating difficulties in producing Form IV Form IV is characterized by the following principal peaks in its X-ray powder diffraction pattern shown below:

| | Peak No. | | | | | | | | | |
|---|---|---|---|---|---|---|---|---|---|---|
| | 1 | 2 | 3 | 4 | 5 | 6 | 7 | 8 | 9 | 10 |
| 2 Theta ° (Cu Kα) | 5.31 | 10.19 | 11.23 | 12.13 | 12.35 | 12.69 | 14.31 | 14.55 | 14.77 | 16.43 |
| d space (Å) | 16.6 | 8.7 | 7.9 | 7.3 | 7.2 | 7.0 | 6.2 | 6.1 | 6.0 | 5.4 |

| | Peak | | | | | | | | | |
|---|---|---|---|---|---|---|---|---|---|---|
| | 11 | 12 | 13 | 14 | 15 | 16 | 17 | 18 | 19 | 20 |
| 2 Theta ° (Cu Kα) | 17.48 | 18.21 | 18.43 | 18.81 | 19.36 | 19.61 | 20.26 | 20.5 | 21.29 | 21.46 |
| d space (Å) | 5.1 | 4.9 | 4.8 | 4.7 | 4.6 | 4.5 | 4.4 | 4.3 | 4.2 | 4.1 |

| | Peak | | | | | | | | | | | |
|---|---|---|---|---|---|---|---|---|---|---|---|---|
| | 21 | 22 | 23 | 24 | 25 | 26 | 27 | 28 | 29 | 30 | 31 | 32 |
| 2 Theta ° (Cu Kα) | 21.95 | 22.53 | 22.77 | 23.38 | 23.59 | 23.9 | 24.45 | 25.02 | 25.56 | 26.19 | 26.83 | 27.21 |
| d space (Å) | 4.0 | 3.9 | 3.9 | 3.8 | 3.8 | 3.7 | 3.6 | 3.6 | 3.5 | 3.4 | 3.3 | 3.3 |

The invention claimed is:

1. The salt (1R,2R,3S,5S)-2-methoxymethyl-3-(3,4-dichlorophenyl)-8-azabicyclo[3.2.1]octane L-tartrate monohydrate.

2. A pharmaceutical composition, comprising a therapeutically effective amount of the salt of claim 1, together with at least one pharmaceutically acceptable carrier, excipient or diluent.

* * * * *